United States Patent [19]

Moran et al.

[11] Patent Number: 4,948,894

[45] Date of Patent: Aug. 14, 1990

[54] 8-FLUORO AND 7, 8, 10-TRIFLUORO-9-(SUBSTITUTED)-6-OXO-6H-BENZO-(C)QUINOLIZINE-5-CARBOXYLIC ACIDS

[75] Inventors: Daniel B. Moran, Suffern; Yang-I Lin, Tappan; Carl B. Ziegler, Pearl River, all of N.Y.

[73] Assignee: American Cyanamid Company, Wayne, N.J.

[21] Appl. No.: 446,747

[22] Filed: Dec. 6, 1989

Related U.S. Application Data

[62] Division of Ser. No. 312,153, Feb. 21, 1989.

[51] Int. Cl.$^5$ .................. C07D 455/04; C07D 401/14; A61K 31/495
[52] U.S. Cl. .................................. 546/95; 544/361
[58] Field of Search ........................... 544/361; 546/95

[56] References Cited

U.S. PATENT DOCUMENTS

| | | | |
|---|---|---|---|
| 4,426,381 | 1/1984 | Matsumura et al. | 544/361 |
| 4,552,879 | 11/1985 | Ishikawa et al. | 544/361 |
| 4,594,347 | 6/1986 | Ishikawa et al. | 544/361 |
| 4,691,016 | 9/1987 | Stern | 546/95 |
| 4,720,495 | 1/1988 | Takagi et al. | 544/361 |

FOREIGN PATENT DOCUMENTS

67666 12/1982 European Pat. Off. ............ 544/361

OTHER PUBLICATIONS

Metscher et al., J. Med. Chem., 21, 485 (1978).
Chu et al., J. Heterocyclic Chem., 24, 1537 (1987).

*Primary Examiner*—Cecilia Shen
*Attorney, Agent, or Firm*—Kenneth J. Dow

[57] ABSTRACT

Novel substituted quinolinecarboxylic acid derivatives of the formula:

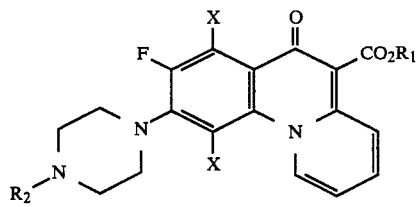

wherein $R^1$ is hydrogen, alkali metal, alkaline earth metal or lower alkyl; $R_2$ is hydrogen, benzyl or alkyl ($C_1$-$C_3$); X is hydrogen or fluoro; which have antibacterial activity, intermediates useful in the preparation of the compounds, methods of producing and using the compounds to treat bacterial infections in animals.

2 Claims, No Drawings

8-FLUORO AND 7, 8, 10-TRIFLUORO-9-(SUBSTITUTED)-6-OXO-6H-BENZO-(C)QUINOLIZINE-5-CARBOXYLIC ACIDS

This is a division of Ser. No. 312,153, filed 2/21/89.

BACKGROUND OF THE INVENTION

The present invention relates to novel substituted quinolinecarboxylic acid derivatives having antibacterial activity.

Since the introduction of nalidixic acid in 1963, a considerable number of patents and scientific papers have been published on compounds having a 1-substituted-1,4 dihydro-4-oxopyridine-3-carboxylic moiety, collectively known as quinolone. Many of these compounds have been shown to have significant antibacterial activity. The structure - activity relationship of quinolone compounds has been reviewed by Schentaget al., Res. Clin. Forums, 7, (2), 9(1985).

At one time it Was believed that substitution at the C-2 position of a substituted quinoline carboxylic acid led to inactive compounds, Metscher et al., J. Med. Chem. 21, 485(1978). However, U.S. Pat. No. 4,426,381 to Matsumura et al., discloses a compound having a thiazoline moiety connecting the C-2 substituent to the N-1 position. This compound Was shown to have good antibacterial activity. Additionally, Chu et al., J. Heterocyclic Chem., 24, 1537(1987) discloses compounds where the C-2 and N-1 positions are bridged by an alkylene chain. The compounds of the present invention comprise novel improvements in which the C-2 and N-1 positions are bridged by an aromatic substituent.

SUMMARY OF THE INVENTION

The present invention relates to new compounds represented by formula I:

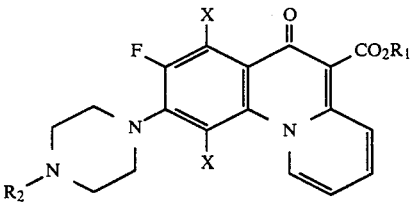

Formula I wherein $R^1$ is hydrogen, alkali metal, alkaline earth metal or lower alkyl; $R_2$ is hydrogen, benzyl or alkyl($C_1$-$C_3$); X is hydrogen or fluoro; and when $R_1$ is hydrogen, the pharmacologically acceptable salts thereof.

Furthermore this invention is concerned with novel compounds represented by the formula II useful for the preparation of compounds of formula I above:

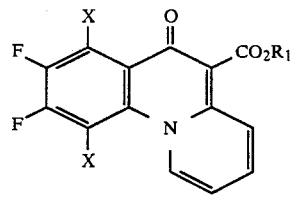

Formula II wherein $R_1$ and X are as defined hereinabove.

In addition, this invention is concerned with novel compounds of formula III.

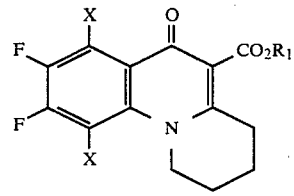

Formula III wherein $R_1$ and X are as defined hereinabove.

DESCRIPTION OF THE INVENTION

The compounds of the present invention may be prepared according to the following reaction scheme.

SCHEME

Scheme

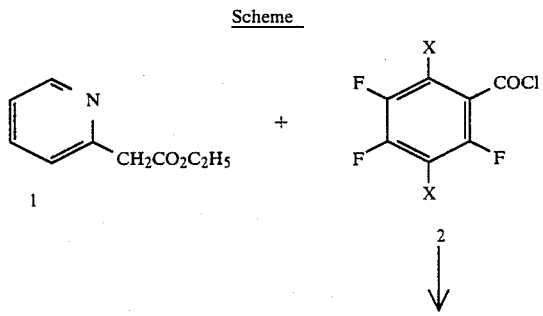

Scheme -continued

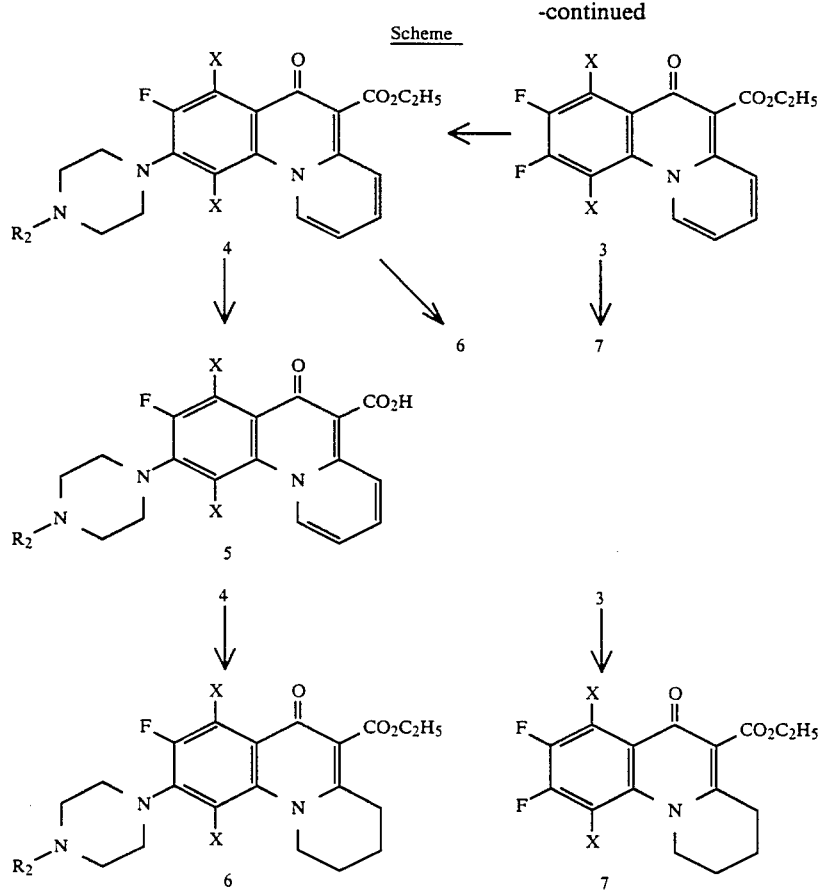

According to the foregoing scheme, ethyl 2-pyridyl acetate 1 is reacted with lithium bis(trimethylsilyl)amide in tetrahydrofuran at −5° C. The mixture is added to acid chloride 2 wherein X is as described above, at −5° C. giving ethyl ester 3. Intermediate 3 is reacted with a substituted piperazine wherein $R_2$ is as described above in N,N dimethylformamide, pyridine or 1-methyl-2-pyrrolidinone at 110° C. giving compound 4. Compound 4 is hydrolyzed with alkali base or acid giving carboxylic acid 5. Also, compound 4 is catalytically reduced with hydrogen using 10% palladium-on-carbon in trifluoroacetic acid giving derivative 6. Ethyl ester 3, wherein X is as described above, is also catalytically reduced with hydrogen using 10% palladium-on-carbon in trifluoroacetic acid giving derivative 7.

The compounds of the present invention are active antibacterial agents as established in the following in vitro tests. As such they are effective in treating bacterial infections in warm-blooded animals.

The in vitro antimicrobial spectrum of the compounds of the invention were determined by the agar plate dilution method with Mueller-Hinton agar and an inoculum of each test organism of approximately $10^4$ colony forming units delivered by the steers replicating device. The minimal inhibitory concentration (MIC) in mcg/ml is defined as the lowest concentration of test compound that inhibited visible growth after 18 hours incubation at 35° C. Results with the test compound described in Example 6 are given in Table I.

TABLE 1
In vitro Antibacterial Spectrum

| Organism and No. | Compound Described In Example No. 6 MIC (mcg/ml) |
|---|---|
| Escherichia coli MOR 84-20 | 2 |
| Escherichia coli VGH 84-19 | 4 |
| Escherichia coli CMC 84-50 | 2 |
| Klebsiella oneumoniae CMC 84-31 | 8 |
| Klebsiella nneumoniae MOR 84-24 | 8 |
| Klebsiella nneumoniae IO 83-5 | 8 |
| Enterobacter cloacae VGH 84-39 | 2 |
| Enterobacter cloacae K 84-10 | 2 |
| Enterobacter cloacae MOR 84-30 | 16 |
| Serratia marcescens MOR 84-41 | 2 |
| Serratia marcescens CMC 83-74 | >16 |
| Serratia marcescens IO 83-63 | 4 |
| Morganella morganii VGH 84-12 | 4 |
| Morganella morganii CMC 84-38 | 0.5 |
| Moroanella morganii MOR 84-45 | 0.5 |
| Proteus rettgeri IO 83-21 | 1 |
| Providencia stuartii CMC 83-3 | >16 |
| Citrobacter diversus K 82-24 | 4 |
| Pseudomonas aeruginosa K 84-16 | >16 |
| Pseudomonas aeruginosa VGH 84-3 | >16 |
| Pseudomonas aeruginosa CMC 83-20 | >16 |
| Staphylococcus aureus VGH 84-47 | >16 |
| Staphylococcus aureus K 82-26 | >16 |
| Staphylococcus aureus CMC 83-131 | >16 |
| Staphylococcus aureus ATCC 25913 | >16 |
| Streptococcus faecalis VCI 85-30 | >16 |
| Streptococcus faecalis VGH 84-69 | >16 |
| Streptococcus faecalis CMC 83-120 | >16 |
| Escherichia coli ATCC 25922 | 4 |
| Escherichia coli D 21 | 4 |
| Escherichia coli D 22 | 2 |

When the compounds are employed for the above utility, they may be combined with one or more pharmaceutically acceptable carriers, for example solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 2 to about 100 mg/kg of animal body weight, preferably given in divided doses two to four times a day, or in sustained release form. For most large mammals the total daily dosage is from about 100 to 750 mg, preferably from about 100 to 500 mg. Dosage forms suitable for internal use comprise from about 100 to 750 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

A decided practical advantage is that these active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the partioular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutioal compositions from the stand-point of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethYlene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The invention will be more fully described in conjunction with the following specific examples which are not to be construed as limiting the scope of the invention.

EXAMPLE 1

2,4,5-Trifluorobenzoio Acid

To a stirred suspension, under argon, of 9 g to magnesium chips in 150 ml of tetrahydrofuran containing a crystal of iodine and cooled to 0° C. was added a solution of 60 g of 2,4,5-trifluorophenyl bromide in 80 ml of tetrahydrofuran dropwise over 1.5 hours. The temperature was kept below 35° C. during the addition and kept at 35° C. for an additional hour then cooled to 0° C. A gentle stream of carbon dioxide was bubbled through the reaction mixture for one hour at 0° C., one hour at room temperature and one hour at reflux. The reaction mixture was cooled to 0° C. and poured into a beaker containing 300 ml of 2N hydrochloric acid and 200 ml of ice water. The aqueous mixture was filtered and the filtrate extracted with $3 \times 335$ ml of methylene chloride. The combined organic extracts were dried and the volatiles removed in vacuo to give 49.4 g of the desired compound. Crystallization from hexanes gave the desired product as light yellow crystals, mp 92°–95° C.

EXAMPLE 2

2,4,5-Trifluorobenzoyl chloride

To a solution of 5.24 g of 2,4,5-trifluorobenzoic acid in 50 ml of ether containing two drops of N,N-dimethylformamide was added, under argon, oxalyl chloride dropwise over 30 minutes. Stirring was continued for an additional 30 minutes when gas evolution ceased. The ether was removed in vacuo and the residue vacuum distilled to give 5.07 g of the desired compound, bp 26°–27° C./0.75 mm.

EXAMPLE 3

Ethyl 8,9-difluoro-6-oxo-6H-benzo[c]quinolizine-5-carboxylate

To a solution of 3.3 g of ethyl 2-pyridyl acetate in 50 ml of dry tetrahydrofuran at $-5°$ C., under argon, was added 25 ml of lithium bis(trimethylsilyl)-amide in hexanes dropwise over 30 minutes. Stirring was continued for an additional 2 hours at $-5°$ C. This mixture was added dropwise, under argon to a $-5°$ C. solution of 3.9 g of 2,4,5 trifluorobenzoyl chloride in 50 ml of dry tetrahydrofuran over one hour. Following an additional hour of stirring the mixture was allowed to slowly reach room temperature. Water ice was added, the resulting solids collected, washed with cold water and dried giving 1.5 g of the desired compound, mp 200°–203° C.

EXAMPLE 4

Ethyl 7,8,9,10-tetrafluoro-6=oxo-6H=benzo[c]-quinolizine-5-carboxylate

A solution of 3.3 g of ethyl 2-pyridyl acetate in 50 ml of dry tetrahydrofuran was cooled to −5° C. and 25 ml of lithium bis(trimethylsilyl)amide in hexanes added dropwise over 30 minutes. Stirring was continued for an additional one hour at −5° C. This mixture was added dropwise under argon to a −5° C. solution of 4.6 g of pentafluorobenzoyl chloride in 50 ml of dry tetrahydrofuran over one hour. Following an additional 3 hours of stirring the mixture was allowed to slowly reach room temperature followed by stirring for 18 hours. The mixture was poured into ice water and extracted with dichloromethane. The separated organic layer was dried and the volatiles removed under vacuum to give a red semisolid which was stirred with acetone, the resulting solid collected, and dried giving 1.28 g of the desired product, mp 198°-200° C.

EXAMPLE 5

Ethyl 8-fluoro-9-(4-methyl-1-piperazinyl)-6-oxo-6H-benzo[c-]quinolizine-5-carboxylate A mixture of 2.0 g of ethyl 8,9-difluoro-6-oxo-6H-benzo[c]quinolizine-5-carboxylate and 3.3 g of N-methylpiperazine was heated at 110° C. for 2 hours. The solvent was evaporated and the residue partitioned between water and dichloromethane. The organic layer was dried and the solvent removed giving 2.0 g of the desired product, mp 167°-170° C.

EXAMPLE 6

8-Fluoro-9-(4-methyl-1-piperazinyl)-6-oxo-6H-benzo[c-]quinolizine-5-carboxylic acid A mixture of 0.38 g of ethyl 8-fluoro-9-(4-methyl-1-piperazinyl)-6-oxo-6H-benzo[c]quinolizine, 25 ml of 0.1N sodium hydroxide and 5 ml of ethyl alcohol was refluxed for 18 hours. The mixture was cooled to room temperature and the pH adjusted to 6 with acetic acid. Most of the volatiles were removed under vacuum to give 0.31 g of water washed and dried desired product, mp 264°-266° C.

EXAMPLE 7

Ethyl 8-fluoro-2,3,4,6-tetrahydro-9-(4-methyl-1-piperazinyl)-6-oxo-1H-benzo[c]quinolizine-5-carboxylate A mixture of 0.35 g of ethyl 8-fluoro-9-(4-methyl-1-piperazinyl)-6-oxo-6H-benzo[c]quinolizine-5-carboxylate and 0.47 g of 10% palladium-on-carbon in 50 ml of trifluoroacetic acid was shaken under 40 lb. of hydrogen in a Parr apparatus for 18 hours. The mixture was filtered and the solvent evaporated. The concentrate was partitioned between aqueous potassium carbonate and dichloromethane. The organic layer was dried and the solvent removed giving 0.32 g of the desired compound, mp 163°-165° C.

EXAMPLE 8

Ethyl 8,9-difluoro-1,2,3,4-tetrahydro-6-oxo-6H-benzo[c-]quinolizine-5-carboxylate A mixture of 0.5 g of ethyl 8,9-difluoro-6-oxo-6H-benzo[c]quinolizine-5-carboxylate and 0.5 g of 10% palladium-on-carbon in 50 ml of trifluoroacetic acid was shaken under 40 lb. of hydrogen in a Parr apparatus for 2 hours. The mixture was filtered and the solvent evaporated. The concentrate was partitioned between aqueous sodium bicarbonate and dichloromethane. The organic layer was dried followed by adding hexanes to give 0.45 g of the desired product, mp 166°-168° C.

What is claimed is:

1. A compound of the formula:

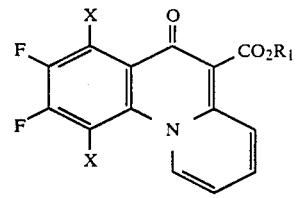

wherein $R_1$ is hydrogen, alkyl($C_1$-$C_3$), alkali metal, or alkaline earth metal and X is hydrogen or fluoro.

2. A process for producing compounds of the formula:

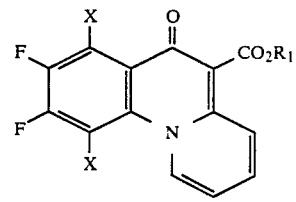

wherein $R_1$ is hydrogen, alkyl($C_1$-$C_3$), alkali metal, or alkaline earth metal and X is hydrogen or fluoro, which comprises reacting ethyl 2-pyridyl acetate with lithium bis(trimethylsilyl)amide in tetrahydrofuran at −5° C. and adding the resultant mixture to either 2,4,5-trifluorobenzoyl chloride or tetrafluorobenzoyl chloride in tetrahydrofuran at −5° C.

* * * * *